United States Patent
Jones et al.

(10) Patent No.: US 6,218,579 B1
(45) Date of Patent: Apr. 17, 2001

(54) PROCESS FOR THE PREPARATION OF ACYLATED CYCLIC 1,3-DICARBONYL COMPOUNDS

(75) Inventors: Robert Oliver Jones; Thomas William Bentley, both of Swansea; Stephen Martin Brown, Huddersfield, all of (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/529,743

(22) PCT Filed: Nov. 17, 1998

(86) PCT No.: PCT/GB98/03458

§ 371 Date: Apr. 18, 2000

§ 102(e) Date: Apr. 18, 2000

(87) PCT Pub. No.: WO99/28282

PCT Pub. Date: Jun. 10, 1999

(30) Foreign Application Priority Data

Nov. 27, 1997 (GB) .................................................. 9725135

(51) Int. Cl.⁷ .................................................. C07C 45/67
(52) U.S. Cl. ........................... 568/309; 568/308; 568/310
(58) Field of Search ..................................... 568/309, 308, 568/310

(56) References Cited

U.S. PATENT DOCUMENTS

| | | | |
|---|---|---|---|
| 4,695,673 | * | 9/1987 | Heather et al. . |
| 4,780,127 | * | 10/1988 | Michaely et al. . |
| 4,806,146 | * | 2/1989 | Carter . |
| 5,886,231 | * | 3/1999 | Brown et al. . |
| 6,096,930 | * | 8/2000 | Ryu et al. . |

FOREIGN PATENT DOCUMENTS

| | | |
|---|---|---|
| 96/22957 | 8/1996 | (WO) . |
| 96/22958 | 8/1996 | (WO) . |

OTHER PUBLICATIONS

Chemical Abstracts, vol. 108, No. 17, 149969d, (1988).

\* cited by examiner

*Primary Examiner*—Johann Richter
*Assistant Examiner*—Sikarl A. Witherspoon
(74) *Attorney, Agent, or Firm*—Dianne Burkhard

(57) ABSTRACT

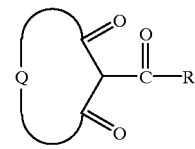

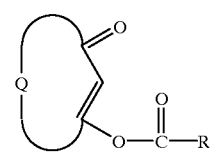

A process for preparing a compound of Formula (I); where Q completes an optionally substituted 5-or 6-member saturated carbocyclic ring and R is optionally substituted phenyl or optionally substituted C3–C6 cycloalkyl which comprises the rearrangement of a compound of Formula (II); where Q and R are as defined in relation to Formula (I) in a polar aprotic, dipolar aprotic or aromatic hydrocarbon solvent in the presence of a moderate base and an azole.

9 Claims, No Drawings

PROCESS FOR THE PREPARATION OF ACYLATED CYCLIC 1,3-DICARBONYL COMPOUNDS

The present invention relates to the production of acylated cyclical 1,3-dicarbonyl compounds and in particular to the production of benzoyl-1,3-cyclohexanediones and cycloalkyl-1,3-cyclohexanediones.

The compounds produced by the process are known as herbicides and plant growth regulators. 2-(Substituted benzoyl)-1,3-cyclohexanediones are known as herbicides from, for example, U.S. Pat. No. 4,780,127, U.S. Pat. No. 4,806,146, U.S. Pat. No. 4,946,981, U.S. Pat. No. 5,006,158, WO 9408988 and WO 9404524. Cyclopropylcarbonylcyclohexanediones are known as plant growth regulators from, for example, EP126713. One method of producing these compounds is by re-arrangement of an enol ester. This method is described in U.S. Pat. No. 4,695,673. This process provides a means to obtain the desired compounds but the process also requires the use of a cyanide source as a catalyst. In WO 9622957 it was shown that in certain solvents the rearrangement of a cyclohexanedione enol ester would proceed in the absence of a cyanide catalyst. However the reactions proceeded much more slowly and produced a lower yield. There is therefore a continuing need for a rearrangement process which produces acceptable yields but which does not use a cyanide catalyst. It has surprisingly been found that azoles may be used in a cyanide-free rearrangement process.

According to the present invention there is provided a process for preparing a compound of Formula (I)

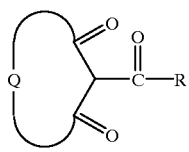
(I)

where Q completes an optionally substituted 5- or 6-member saturated carbocyclic ring and R is optionally substituted phenyl or optionally substituted $C_3$–$C_6$ cycloalkyl which process comprises the rearrangement of a compound of Formula (II)

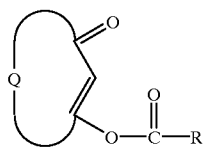
(II)

where Q and R are as defined in relation to Formula (I) in a polar aprotic, dipolar aprotic or aromatic hydrocarbon solvent in the presence of a moderate base and an azole.

The compounds of formula (I) may exist as one or more of the structural formulae shown below because of tautomerism.

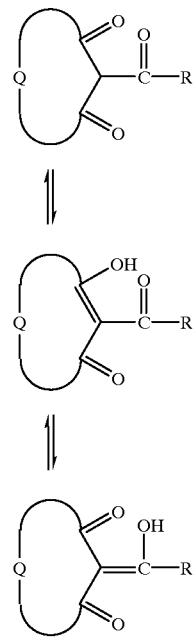

The values of Q and R are as defined above.

The term "azole" refers to a five membered nitrogen-containing ring which is optionally substituted and which may be fused to other rings.

Optional substituents for the carbocyclic ring formed by Q include $C_{1-4}$ alkyl, $C_{1-4}$ haloalkyl, $C_{1-4}$ alkoxy, $C_{2-5}$ alkylene (in which case the compounds have a spiro structure) $COC_{1-4}$ alkyl, COOH, $COOC_{1-4}$ alkyl, phenyl, halophenyl, $C_{1-4}$ haloalkylphenyl, phenoxy halophenoxy, $C_{1-4}$ haloalkylphenoxy, or heterocyclic groups such as pyridyl or pyrimidinyl.

Optional substituents for the phenyl and cycloalkyl rings R include halogen, cyano, $NO_2$, $C_{1-4}$ alkyl, $C_{1-4}$ haloalkyl, $C_{1-4}$ alkoxy, phenoxy, halogen substituted phenoxy, $C_{1-4}$ haloalkyl substituted phenoxy, $R^bS(O)_nO_m$ in which m is 0 or 1, n is 0, 1 or 2 and $R^b$ is $C_{1-4}$ alkyl, $C_{1-4}$ haloalkyl, phenyl or benzyl, $NHCOR^c$ in which $R^c$ is $C_{1-4}$ alkyl, $NR^dR^e$ in which $R^d$ and $R^e$ independently are hydrogen or $C_{1-4}$ alkyl; $R^fC(O)$— in which $R^f$ is hydrogen, $C_{1-4}$ alkyl, $C_{1-4}$ haloalkyl or $C_{1-4}$ alkoxy; $SO_2NR^gR^h$ in which $R^g$ and $R^h$ independently are hydrogen or $C_{1-4}$ alkyl; or any two adjacent substituents together with the carbon atoms to which they are attached form a 5 or 6 membered heterocyclic ring containing up to three heteroatoms selected from O, N or S and which may be optionally substituted by $C_{1-4}$ alkyl, $C_{1-4}$ haloalkyl, $C_{1-4}$ alkoxy, $=NOC_{1-4}$ alkyl or halogen.

As used herein the term "alkyl", refers to straight or branched chains. The term "haloalkyl" refers to an alkyl group substituted by at least one halogen. Similarly the term "haloalkoxy" refers to an alkoxy group substituted by at least one halogen. As used herein the term "halogen" refers to fluorine, chlorine, bromine and iodine.

As used herein the term "aryl" refers to aromatic carbocyclic ring systems such as phenyl or naphthyl, especially phenyl.

A preferred carbocyclic ring formed by Q is an optionally substituted cyclohexanedione.

One class of compounds of formula (I) is cyclohexanediones of formula (IA)

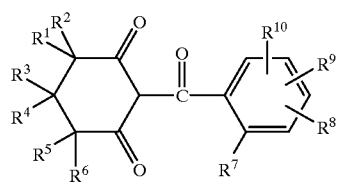

(IA)

in which $R^1$, $R^2$, $R^3$, $R^4$, $R^5$ and $R^6$ are independently hydrogen or $C_{1-6}$ alkyl; $R^7$ is hydrogen, halogen, cyano, $NO_2$, $C_{1-4}$ alkyl, $C_{1-4}$ haloalkyl, $C_{1-4}$ alkoxy or $R^aS$ in which $R^a$ is $C_{1-4}$ alkyl; $R^8$, $R^9$ and $R^{10}$ independently are hydrogen, halogen, $C_{1-4}$ alkyl, $C_{1-4}$alkoxy, $C_{1-4}$ haloalkyl, $C_{1-4}$ haloalkoxy, CN, $NO_2$, phenoxy, phenoxy, halophenoxy or $C_{1-4}$ haloalkylphenoxy; $R^bS(O)_n$ Om in which m is 0 or 1, n is 0, 1 or 2 and $R^b$ is $C_{1-4}$ alkyl, $C_{1-4}$ haloalkyl, phenyl or benzyl, $NHCOR^c$ in which $R^c$ is $C_{1-4}$ alkyl, $NR^dR^e$ in which $R^d$ and $R^e$ independently are hydrogen or $C_{1-4}$ alkyl; $R^fC(O)$— in which $R^f$ is hydrogen, $C_{1-4}$ alkyl, $C_{1-4}$ haloalkyl or $C_{1-4}$ alkoxy; $SO_2NR^gR^h$ in which $R^g$ and $R^h$ independently are hydrogen or $C_{1-4}$ alkyl; or any two of $R^8$, $R^9$ and $R^{10}$ together with the carbon atoms to which they are attached form a 5 or 6 membered heterocyclic ring containing up to three heteroatoms selected from O, N or S and which may be optionally substituted by $C_{1-4}$ alkyl, $C_{1-4}$ haloalkyl, $C_{1-4}$ alkoxy, $=NOC_{1-4}$ alkyl or halogen which are prepared from compounds of formula (IIA)

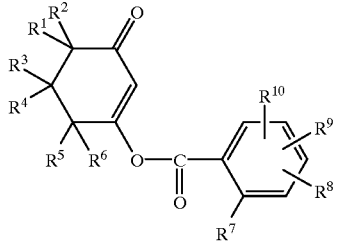

(IIA)

where $R^1$, $R^2$, $R^3$, $R^4$, $R^5$, $R^6$, $R^7$, $R^8$, $R^9$ and $R^{10}$ are as defined in relation to Formula (IA).

A preferred group of compounds of Formula (IA) are those where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or $R^aS$ in which $R^a$ is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $R^bS(O)n$ Om in which m is 0 or 1, n is 0, 1 or 2 and $R^b$ is $C_{1-4}$ alkyl, $C_{1-4}$ haloalkyl, phenyl or benzyl, $NHCOR^c$ in which $R^c$ is $C_{1-4}$ alkyl, $NR^dR^e$ in which $R^d$ and $R^e$ independently are hydrogen or $C_{1-4}$ alkyl; $R^fC(O)$— in which $R^f$ is hydrogen, $C_{1-4}$ alkyl, $C_{1-4}$ haloalkyl or $C_{1-4}$ alkoxy; or $SO_2NR^gR^h$ in which $R^g$ and $R^h$ independently are hydrogen or $C_{1-4}$ alkyl.

Preferably $R^1$, $R^2$, $R^3$, $R^4$, $R^5$ and $R^6$ are independently hydrogen or $C_{1-4}$ alkyl. More preferably $R^1$, $R^2$, $R^5$ and $R^6$ are hydrogen and $R^3$ and $R^4$ are independently hydrogen or methyl, especially hydrogen.

$R^7$ is preferably halogen or $NO_2$. A preferred value for $R^8$ is hydrogen.

$R^9$ is preferably hydrogen or $C_{1-4}$ alkoxy, especially ethoxy. Most preferably $R^9$ is hydrogen.

Preferably $R^{10}$ is a group $R^bS(O)_nOm$ where $R^b$, n and m are as defined above. More preferably m is zero, n is 2 and $R^b$ is $CH_3$ or $C_2H_5$. Most preferably $R^{10}$ is a group $CH_3SO_2$ attached to the benzoyl group at the 4-position.

The most preferred compounds of Formula (IA) are 2-(2-chloro-4-methanesulphonylbenzoyl)-1,3-cyclohexanedione and 2-(2-nitro-4-methanesulphonylbenzoyl)-1,3-cyclohexanedione Another class of compounds of formula (I) are compounds of formula (IB)

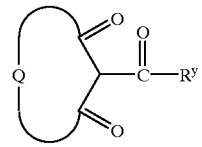

(IB)

where Q is as defined in relation to Formula (I) and $R^y$ is C3-6 cycloalkyl optionally substituted by one more groups $R^z$ where $R^z$ is as defined for $R^7$ above. A preferred group $R^y$ is optionally substituted cyclopropyl. A preferred compound of Formula (IB) is trinexepac ethyl (ethyl 4-cyclopropyl (hydroxy)methylene-3,5-dioxocyclohexanedionecarboxylate).

Preferred azoles are compounds of Formula (III)

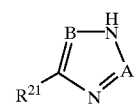

(III)

in which A is N or $CR^{22}$; B is N or $CR^{23}$; $R^{21}$, $R^{22}$ and $R^{23}$ are independently H, alkyl, or aryl or when B is $CR^{23}$, $R^{21}$, and $R^{23}$ together with the carbon atoms to which they are attached form a 6-membered carbocyclic ring; and salts thereof A is preferably N or CH.

Preferably B is N and $R^{21}$ is H or B is $CR^{23}$ and $R^{21}$ and $R^{23}$ together with the carbon atoms to which they are attached form a 6-membered unsaturated carbocyclic ring.

Particularly preferred compounds of Formula (III) are 1H-1,2,4-triazole and 1H-1,2,3-benzotriazole.

Suitable salts of azoles may be for example the potassium salt or the tetrabutylammonium salt.

The azole is used in an amount up to about 50 mole percent based on the enol ester. Generally about 1–10 mole % of the azole is preferred The process is conducted with a molar excess, with respect to the enol ester compound of Formula (II), of a moderate base. By the term "moderate base" is meant a substance which acts as a base yet whose strength of activity as a base lies between that of strong bases such as hydroxides (which could cause hydrolysis of the enol ester) and that of weak: bases such as N,N-dimethylaniline (which would not function effectively). Moderate bases suitable for use in this embodiment include both organic bases such as trialkylamines and inorganic bases such as alkali metal carbonates and phosphates. The trialkylamines are preferably tri(lower alkyl) amines having from 1 to 6, preferably 1 to 4 carbon atoms per alkyl group. A particularly preferable amine is triethylamine. Suitable inorganic bases include sodium carbonate, potassium carbonate and trisodium phosphate. Even a bicarbonate such as potassium bicarbonate will function effectively in this reaction when used in combination with a dipolar aprotic solvent such as dimethylformamide. The base is used in an amount of from about 1 to about 4 moles per mole of enol ester, preferably about 2 moles per mole. A preferred base is an inorganic base especially potassium carbonate.

A number of different solvents may be usable in this process, depending on the nature of the reactants. Suitable solvents are polar aprotic solvents (such as acetonitrile, cyclic ethers such as tetrahydrofuran, linear ethers such as 1,2dimethoxyethane, ketones such as methyl isobutyl ketone or esters such as alkyl acetates for example ethyl acetate); dipolar aprotic solvents (such as dimethylformamide, dimethylsulphoxide and dmac) and aromatic hydrocarbons (including alkylated hydrocarbons such as toluene, xylene, cumene, and cymene and halogenated hydrocarbons such as chlorobenzene). Preferred solvents are polar aprotic solvents, dipolar aprotic solvents and aromatic hydrocarbons, especially polar aprotic or dipolar solvents A particularly preferred solvent is acetonitrile.

Depending on the choice of reactants and in particular the choice of solvents a phase catalyst may also be employed. The selection of a suitable phase transfer catalyst can be determined by routine procedures well known to the skilled chemist. Known phase transfer catalysts include tetralkyl ammonium halides and phosphonium salts. Preferred catalysts are tetralkyl ammonium halides, especially tetrabutyl ammonium bromide, tetrabutyl ammonium chloride, cetyltrimethyl ammonium bromide or cetyltrimethyl ammonium chloride. The phase transfer catalyst is generally used at 1–10 mol %.

If the choice of reaction conditions require the use of a phase-transfer catalyst, the catalyst may still be omitted by use of a suitable salt of the azole e.g. the tetrabutyl ammonium salt.

In one embodiment the process is carried out in a non-polar solvent, in the presence of a moderate inorganic base and a phase transfer catalyst.

In general, depending on the nature of the reactants and the azole, the rearrangements may be conducted at temperatures from −10C, up to about 100° C., preferably 0–60° C., most preferably 20–40° C. In some cases, for instance when there is a possible problem of excessive by-product formation (for instance, when using an orthonitro benzoyl halide) the temperature should be kept at about 40° C. maximum.

Depending on the nature of the reactants and more especially the nature of the solvent used in the reaction, water may be added to the reaction medium. In general it has been found that the amount of water should not exceed 0.2 w/w % of the whole system or 0.1 mol/mol based on the substrate.

The process may be carried out using the enol ester as the starting material, or with generation of the enol ester in situ, for instance for the preparation of compounds of Formula (IA) by reaction of a compound of Formula (IV)

(IV)

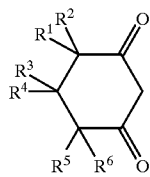

where $R^1$, $R^2$, $R^3$, $R^4$, $R^5$ and $R^6$ are as defined in relation to Formula (IA) with a compound of Formula (V)

(V)

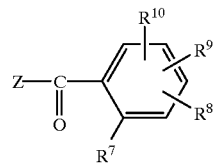

where $R^7$, $R^8$, $R^9$ and $R^{10}$ are as defined in relation to Formula (IA) and Z is a halo, preferably chloro.

When the enol ester is utilised as a starting material it may be prepared by any of a number of known means. For example when preparing compounds of formula (IA), the appropriate enol ester is formed by acylation of a compound of Formula (IV) with, a compound of Formula (V).

The enol ester may be isolated from the resulting product mix by known techniques, for instance washing the resultant solution with acid and base, and with saturated sodium chloride solution, and drying. Such a technique is advantageous when a different solvent is preferred for the rearrangement of the enol ester to the compound of Formula (I). The dried enol ester may be mixed with an appropriate solvent such as acetonitrile, 1,2-dichloroethane, or toluene and contacted with the appropriate amounts of azole, base and, optionally, phase transfer catalyst and, if required, heated to the desired temperature, to produce the final product.

The production of compounds of Formula (I) according to the invention maybe advantageously carried out starting with compounds such as those of Formula (IV) and Formula (V) and may be carried out without isolation of the intermediate enol ester (II). Thus the compound of Formula (IV) and the compound of Formula (V) are reacted in the presence of a base such as an alkali or alkaline earth metal carbonate.

The rearrangement reaction proceeds via an intermediate of Formula (VI)

(VI)

where R is as defined in relation to Formula (I) and Y is the residue formed with the azole. When compounds of Formula (IA) are being prepared the rearrangement reaction proceeds via an intermediate of Formula (VIA)

(VIA)

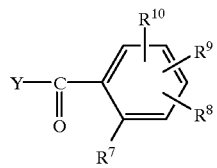

where $R^7$, $R^8$, $R^9$ and $R^{10}$ are as defined in relation to Formula (IA) and Y is the residue formed with the azole.

The compounds of Formula (VI) may be isolated by standard techniques such as filtration or extraction into a solvent such as dichloromethane and removal of the solvent by evaporation. To prepare compounds of formula (IA) compounds of Formula (VIA) may then be reacted with compounds of Formula (IV)

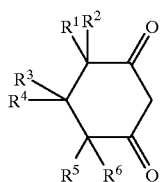

(IV)

in the presence of a solvent and a base to yield the final product.

Certain compounds of Formula (VI) are novel and as such form a further aspect of the invention. In particular novel compounds of formula (VII) are compounds of formula (VIA) where Y is a 1,2,4-triazolyl or a 1,2,3-benzotriazolyl group and $R^7$, $R^8$, $R^9$ and $R^{10}$ are as defined in relation to Formula (IA) provided that when Y is 1,2,4-triazolyl and $R^7$ is halo, $C_{1-4}$ alkyl, $C_{1-4}$ haloalkyl, $C_{1-4}$ alkoxy, nitro or cyano, then none of $R^8$, $R^9$ or $R^{10}$ may be halo, $C_{1-4}$ alkyl, $C_{1-4}$ haloalkyl, $C_{1-4}$ alkoxy, nitro or cyano at the 6-position of the phenyl ring.

In a preferred alternative the enol ester of Formula (II) may be retained in the reaction mass formed from a reaction of a compound of Formula (IV) with a compound of Formula (V) by adding an azole, water and additional base if necessary and then retaining the intermediate of Formula (VI) in the reaction mass and continuing the reaction to produce the compound of Formula (IA). Most preferably all stages are carried out using the same solvent.

Comparable yields can be obtained either with or without isolation of the enol ester of Formula (II) and/or the isolation of compounds of Formula (VI).

The compound of Formula (I) is obtained from this reaction in the form of its salt.

The desired acylated compound of Formula (I) may be obtained with acidification and extraction with an appropriate solvent.

Compounds of formula (II), (III), (IV) and (V) are known compounds or may be produced from known compounds by known methods.

The process of the invention is illustrated by the following examples.

EXAMPLE 1

2-benzoyl-1,3-cyclohexanedione from the acid chloride.

A mixture of 1,3-Cyclohexanedione (2.31 g), potassium carbonate (1.5 g) and acetonitrile (20 ml) were stirred at 35° C. for 3 hrs. To the resulting suspension was added benzoylchloride (1.5 g) over a few minutes and the mixture was stirred for 30 minutes. Potassium carbonate (2 g) and 1,2,4-triazole (0.035 g) were then added and the mixture was stirred at 35° C. for 16 hrs. After this time the reaction mixture was evaporated under reduced pressure, the mixture dissolved in water and acidified with HCl to precipitate the product. Extraction into chloroform and evaporation gave a 90% yield of 2-benzoyl-1,3-cyclohexanedione.

EXAMPLE 2

2-(2-Chloro-4-methanesulphonylbenzoyl)-1,3-cyclohexanedione from the acid chloride. 2-Chloro-4-methanesulphonylbenzoyl chloride (5 g) was prepared by the reaction of 2-chloro-4-methanesulphonylbenzoic acid with thionyl chloride. The acid chloride was dissolved in acetonitrile (40 ml). A mixture of 1,3-cyclohexanedione (2.24 g), potassium carbonate (6.9 g) and acetonitrile (40 ml) was stirred at room temperature for 4 hours. To this solution was added the acid chloride solution over 10 min and allowed to stir 1 hour. 1,2,4-Triazole (0.07 g) was then added and the mixture allowed to stir 16 hours at room temperature. The solvent was removed and the residue was dissolved in water and acidified. The product was extracted into dichloromethane and the solvent was dried then evaporated to give the desired product in 83.6% yield.

EXAMPLE 3

2-benzoyl-1,3-cyclohexanedione from the enol ester.

3-(benzoyloxy)-2-cyclohexen-1-one (2.32 g), potassium carbonate (1.99 g), 1,2,4-triazole (0.034 g) and acetonitrile (20 ml) were placed in a 50 ml round-bottomed flask containing a magnetic follower. The flask was stoppered and placed in a 35° C. thermostatted bath. The white suspension/solution in the flask was then stirred rapidly and periodically the stirring was stopped for HPLC analysis samples to be taken. After 2 hours the reaction mixture had turned yellow and 45% of the enol ester had reacted to form 2-benzoyl-1,3-cyclohexanedione and benzoyl triazole. The reaction mixture had also thickened slightly, but was not immobile. After 6 hours the reaction was complete by HPLC with all enol ester and benzoyl triazole used up.

The solvent was removed on a rotary evaporator to leave a yellow solid which was dissolved in water (100 ml) and the solution acidified with aqueous HCl to pH 2.8 (3 1ml of 1 M HCl) to precipitate 2-benzoyl-1,3-cyclohexanedione. The suspension was then extracted with chloroform (2×50 ml), the chloroform extracts dried (magnesium sulphate), and the solvent removed to leave the desired product. Yield 2.07 g, 89.1%.

EXAMPLE 4

2-(2-nitro-4-methanesulphonylbenzoyl)-1,3-cyclohexanedione 3-(2-nitro-4-methanesulphonylbenzoyloxy)-2-cyclohexen-1-one (2.0 g), potassium carbonate (1.22 g), solvent (20 ml), 1,2,4-triazole (0.02 g) and a phase transfer catalyst (5 mol %) were placed in a reaction tube. The mixture was stirred at 57° C. and the amount of product (2-(2-nitro-4-methanesulphonylbenzoyl)-1,3-cyclohexanedione) determined over a period of time. The results are set out in the Table below.

| Solvent | PTC | Time | Yields (% theory) | | |
| --- | --- | --- | --- | --- | --- |
| | | | Triketone | Enol Ester | Hydrolysis |
| Toluene | — | 6 hours | 1.1 | 98 | — |
| Toluene | TBAB | 5 hours | 69.0 | 10 | 13 |
| Toluene | CTAB | 5 hours | 71 | 2 | 22 |
| MiBk | — | 5 hours | 70 | 0 | 25 |

Triketone=2-(2-nitro-4-methanesulphonylbenzoyl)-1,3-cyclohexanedione
Enol ester=3-(2-nitro-4-methanesulphonylbenzoyloxy)-2-cyclohexen-1-one
PTC=phase transfer catalyst
TBAB=tetrabutylammonium bromide
CTAB=cetyltrimethylammonium bromide
CHD=1,3-cyclohexanedione
MiBk=methyl isobutyl ketone

EXAMPLE 5

2-(2-nitro-4-methanesulphonylbenzoyl)-1,3-cyclohexanedione 3-(2-nitro-4-methanesulphonylbenzoyloxy)-2-cylohexen-1-one (1 g), potassium carbonate (0.61 g), 1,2,4-triazole (0.01 g), tetrabutylammonium bromide (see below) and acetonitrile (10 ml) were stirred 20° C. After the reaction period, the solvent was removed under reduced pressure and the residue was dissolved in water. Acidification with HCl, extraction into diethyl ether and evaporation gave 2-(2-nitro-4-methanesulphonylbenzoyl) 1,3-cyclohexanedione.

With 30 mol % tetrabutylammonium bromide, the reaction gave a 93% yield after 2.5 hours. Without tetrabutylammonium bromide, the reaction gave 85% yield and 15% hydrolysis after 12 hours.

EXAMPLE 6

2-Chloro-4-methanesulphonyl benzoyltriazolamide

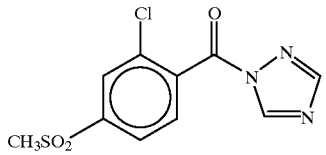

2-Chloro-4-methanesulphonylbenzoic acid (2.355 g) was suspended in toluene (150 ml) and dimethylformamide (0.1 ml) was added via a syringe. The suspension was heated to 75° C., then thionyl chloride (0.8 ml) in toluene (10 ml) added over 30 minutes. The suspension was heated for 1 hour to effect reaction, refluxed for 1 hour to remove acidic gases, then added via a cannula to a stirred suspension of 1,2,4-triazole (1.390 g) in toluene. The resultant suspension was stirred at room temperature for 48 hours then filtered. The precipitate was extracted with dichloromethane, and the solvent removed under reduced pressure to afford the title compound as a colourless powder (1.635 g, 57.4%). Recrystalisation from ethyl acetate produced the compound as colourless spines.

1H NMR (200 MHz, CDCl3): 9.14 (1H,s,NCH), 8.12 (1H, d, J 1.5 Hz. $H_3$) 8.09 (1H, s, NCH), 8.02 (1H.dd, J 8.1.J' 1.6 Hz, $H_5$), 7.79 (1H,d,J 8.1 Hz, $H_6$), 3.16 (3H,s,Me). 13C NMR (200 MHz, CDCl3): 163.82, 154.04, 144.65, 144.57, 136.32, 134.54, 130.78, 129.20, 125.77, 44.33.

EXAMPLE 7

2-Nitro-4-methanesulphonyl benzoyltriazolamide

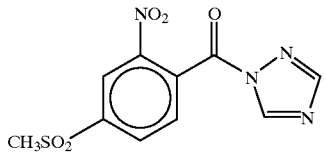

2-Nitro-4-methanesulphonylbenzoic acid (5.12 g), was suspended in 50/50 w/w xylene/acetonitrile (300 ml) and dimethylformamide (0.1 ml), added via a syringe. The suspension was heated to 75° C., then thionyl chloride (1.7 ml), in xylene (10 ml) added over 30 minutes. The suspension was heated for 6 hours to effect reaction, then added via a cannula to a stirred suspension of 1,2,4-triazole (2.918 g), in 50/50 w/w xylene/acetonitrile (100 ml). The resultant suspension was stirred at room temperature for 15 hours, filtered, and the solvent removed under reduced pressure to afford the title compound as a pale yellow powder (3.53 g, 56.8%). Recystallisation from ethyl acetate yielded the compound as colourless plates.

1H MNR (200 MHz, d6.acetone): 9.40 (1H,s,NCH), 8.83 (1H, d, J 1.5 Hz, H3), 8.59 (1H, dd, J8.1, J' 1.7 Hz, H5) 8.26 (1H, d,J 7.9 Hz$H_6$), 8.14 (1H,s,NCH), 3.41 (3H,s,Me): 13C NMR (200 MHz, d6. acetone): 163.57, 154.87, 147.77, 145.97, 145.63, 134.47, 133.46, 132.37, 124.51, 43.94.

EXAMPLE 8

2-(2-Chloro-4-methanesulphonyl benzoyl)cyclohexan-1,3-dione,

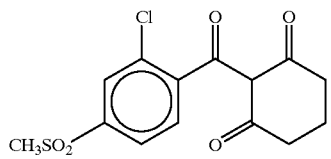

1-(2-chloro-4-methanesulphonylbenzoyl)-1,2,4-triazole (388 mg), cyclohexan-1,3-dione (161 mg) and potassium carbonate (259 mg) were suspended in acetonitrile (30 ml) and stirred overnight. The acetonitrile was removed under reduced pressure, the residue dissolved in water (100 ml) and acidified with 1M hydrogen chloride solution to pH 1.5. The solution was extracted with dichloromethane, dried (magnesium sulfate), filtered and the solvent removed under reduced pressure to afford the title compound as a pale yellow solid (0.263 g, 55.6%). $^1$H NMR (200 Mhz, CDCl3); 7.88–8.01 (2H,m,Ph), 7.36–7.40 (1H, m, Ph), 3.11 (3H,s, Me), 2.68–2.76(2H,m,CH2C=O), 2.37–2.47 (2H,m, CH$_2$C=O), 1.97–2.18(2H,m,CH2—CH2).

EXAMPLE 9

2-(2-nitro-4-methanesulphonyl benzoyl)cyclohexan-1,3-dione

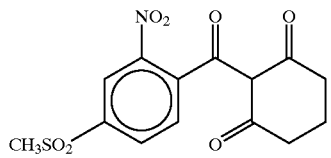

1-(2-Nitro-4-methanesulphonylbenzoyl)-1,2,4-triazole (666 mg), cyclohexan-1,3-dione (254 mg) and potassium carbonate (419 mg, 1.8 mmol, 1.4 equiv) were suspended in acetonitrile (30 ml) and stirred overnight. The acetonitrile was removed under reduced pressure, the residue dissolved in water (100 ml) and acidified with 1 M hydrogen chloride solution to pH 1.5. The solution was extracted with dichloromethane, dried (magnesium sulfate), filtered and the solvent removed under reduced pressure to afford the title compound as a pale yellow solid (0.789g, quant).

$^1$H NMR (200 Mhz, CDCl$_3$); 8.74 (1H,s,H6); 8.26(1H,d, J 8.1 Hz, Ph); 7.46 (1H, d, J 7.86 Hz, Ph), 3.16 (3H, s, Me), 2.83 (2H,t, J 6.3Hz, CH2—C=O), 2.36 (2H,t, J 6.5 Hz, CH2—C=O), 2.00–2.12 (2H,m, CH$_2$CH$_2$).

$^{13}$C NMR (200 Mhz, CDCl$_3$); 195.86; 194.26; 145.66; 142.04; 141.17; 132.76; 128.26; 123.23; 112.69; 44.37; 37.24; 31.63; 19.11.

What is claimed is:

1. A process for preparing a compound of Formula (I):

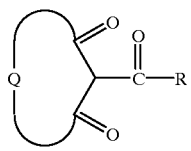

(I)

where Q completes an optionally substituted 5- or 6member saturated carbocyclic ring and R is optionally substituted phenyl or optionally substituted $C_3$–$C_6$ cycloalkyl which process comprise the rearrangement of a compound of Formula (II)

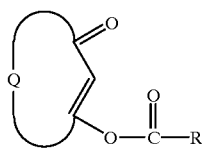

(II)

where Q and R are as defined in relation to Formula (I) in a polar aprotic, dipolar aprotic or aromatic hydrocarbon solvent in the presence of a moderate base and an azole compound of Formula (III)

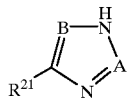

(III)

in which A is N or $CR^{22}$; B is N or $CR^{23}$ and $R^{21}$, $R^{22}$ and $R^{23}$ are independently H, alkyl, or aryl or when B is $CR^{23}$, $R^{21}$ and $R^{23}$ together with the carbon atoms to which they are attached form a 6-membered carbocyclic ring and salts thereof.

2. A process according to claim 1 wherein the compound of formula (I) is a compound of formula (IA)

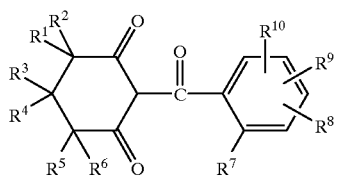

(IA)

where $R^1$, $R^2$, $R^3$, $R^4$, $R^5$ and $R^6$ are independently hydrogen or $C_{1-4}$ alkyl; $R^7$ is halogen, cyano, $NO_2$, $C_{1-4}$ alkyl, $C_{1-4}$ haloalkyl, $C_{1-4}$ alkoxy or $R^aS$ in which $R^a$ is $C_{1-4}$ alkyl; $R^8$, $R^9$ and $R^{10}$ independently arm hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy, halophenoxy, $C_{1-4}$ haloalkylphenoxy; $R^bS(O)n$ Om in which m is 0 or 1, n is 0, 1 or 2 and $R^b$ is $C_{1-4}$ alkyl, $C_{1-4}$ haloalkyl, phenyl or benzyl, $NHCOR^c$ in which $R^c$ is $C_{1-4}$ alkyl, $NR^dR^e$ in which $R^d$ and $R^e$ independently are hydrogen or $C_{1-4}$ alkyl; $R^fC(O)$— in which $R^f$ is hydrogen, $C_{1-4}$ alkyl $C_{1-4}$ haloalkyl or $C_{1-4}$ alkoxy; $SO_2NR^gR^h$ in which $R^g$ and $R^h$ independently are hydrogen or $C_{1-4}$ alkyl; or any two of $R^8$, $R^9$ and $R^{10}$ together with the carbon atoms to which they are attached form a 5 or 6 membered heterocyclic ring containing up to three heteroatoms selected from O, N or S and which may be optionally substituted by =$NOC_{1-4}$ alkyl, $C_{1-4}$ alkyl, $C_{1-4}$ haloalkyl, $C_{1-4}$ alkoxy or halogen; and the compound of formula (II) is a compound of formula (IIA)

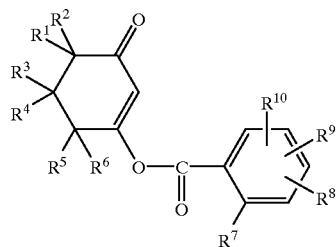

(IIA)

where $R^1$, $R^2$, $R^3$, $R^4$, $R^5$, $R^6$, $R^7$, $R^8$, $R^9$ and $R^{10}$ as defined for formula (IA).

3. A process according to claim 2 where $R^1$, $R^2$, $R^3$, $R^4$, $R^5$ and $R^6$ are independently hydrogen or $C_{1-6}$ alkyl; $R^7$ is halogen, cyano, $NO_2$, $C_{1-4}$ alkyl, $C_{1-4}$ haloalkyl, $C_{1-4}$ alkoxy or $R^aS$ in which $R^a$ is $C_{1-4}$ alkyl; $R^8$, $R^9$ and $R^{10}$ independently are hydrogen, halogen, $C_{1-4}$ alkyl, $C_{1-4}$ alkoxy, $C_{1-4}$ haloalkyl, $C_{1-4}$ haloalkoxy, CN, $NO_2$, phenoxy or substituted phenoxy; $R^bS(O)n$ Om in which m is 0 or 1, n is 0, 1 or 2 and $R^b$ is $C_{1-4}$ alkyl, $C_{1-4}$ haloalkyl, phenyl or benzyl, $NHCOR^c$ in which $R^c$ is $C_{1-4}$ alkyl, $NR^dR^e$ in which $R^d$ and $R^e$ independently are hydrogen or $C_{1-4}$ ; $R^fC(O)$— in which $R^f$ is hydrogen, $C_{1-4}$ alkyl, $C_{1-4}$ haloalkyl or $C_{1-4}$ alkoxy; or $SO_2NR^gR^h$ in which $R^g$ and $R^h$ independently are hydrogen or $C_{1-4}$alkyl.

4. A process according to claim 2 where $R^1$, $R^2$, $R^5$ and $R^6$ are hydrogen and $R^3$ and $R^4$ are independently hydrogen or methyl.

5. A process according to claim 2 where $R^7$ is halogen or $NO_2$, $R^8$ is hydrogen, $R^9$ is hydrogen or $C_{1-4}$ alkoxy and $R^{10}$ is a group $CH_3SO_2$ attached to the benzoyl group at the 4-position.

6. A process according to claim 1 where the azole compound of formula (III) is 1,2,4-triazole or 1,2,3-benztriazole.

7. A process according to claim 1 wherein the process is carried out in the presence of a phase transfer catalyst.

8. A process according to claim 7 where the phase transfer catalyst is tetrabutyl ammonium bromide.

9. A process according to claim 1 where the moderate base is an inorganic base.

* * * * *